(12) United States Patent
Shimkets (10) Patent No.: US 6,489,109 B1
(45) Date of Patent: Dec. 3, 2002

(54) TRANSCRIPTION-BASED GENE MAPPING

(75) Inventor: Richard A. Shimkets, West Haven, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/586,701

(22) Filed: Jun. 1, 2000

Related U.S. Application Data (60) Provisional application No. 60/137,307, filed on Jun. 3, 1999.

(51) Int. Cl.$^7$ .......................... C12Q 1/68; C12P 19/34; C07H 21/04; C07H 21/02; C12N 9/16; C12N 15/00

(52) U.S. Cl. .................... 435/6; 435/91.1; 435/91.2; 435/325; 435/196; 536/23.1; 536/24.32; 536/24.33

(58) Field of Search ........................ 435/6, 325, 91.1, 435/91.2, 196; 536/23.1, 24.3, 24.33; 364/167.01; 422/68.1

(56) References Cited

U.S. PATENT DOCUMENTS 5,871,697 A * 2/1999 Rothberg et al. .......... 422/68.1

FOREIGN PATENT DOCUMENTS

WO          WO 99/07896        *   2/1999

OTHER PUBLICATIONS

Mancin Et Al.. Selection and Fine Mapping of Chromosome-specific cDNAs: Application to human Chromosome 1. Genomic, vol. 38, pp. 149–154, Dec. 1996.*

Watanabe et al. Nature Genetics, /a radiaition hybrid map of the rat genome containing 5,255 markers. Nature Genetics, vol. 22, pp. 27–36, May 1996.*

Walter et al. A method for constructing radiation hybrid maps of whole genomes. Nature Genetics, vol. 7, pp. 22–28, May 1994.*

Chelly et al. Illegitimate (or Ectopic) transcription proceeds through the usual promoters. Biochemical and Biophysical Research communications, vol. 178, No. 2, pp., 553–557, Dec. 1991.*

Houlgatte, et al. (1995). "The Genexpress Index: A Resource for Gene Discovery and the Genic Map of the Human Genome." *Genome Res.* 5: 272–304.

International Search Report. PCT/US 00/40033. Issued on May 12, 2001.

Boehnke et al. (1991). "Statistical methods for multipoint radiation hybrid mapping." *Am J Hum Genet* 49(6): 1174–88.

Cox et al. (1990). "Radiation hybrid mapping: a somatic cell genetic method for constructing high–resolution maps of mammalian chromosomes." *Science* 250(4978): 245–50.

Cuthbert et al. (1995). "Construction and characterization of a highly stable human: rodent monochromosomal hybrid panel for genetic complementation and genome mapping studies." *Cytogenet Cell Genet* 71(1): 68–76.

Gyapay et al. (1996). "A radiation hybrid map of the human genome." *Hum Mol Genet* 5(3): 339–46.

Khan et al. (1992). "Single pass sequencing and physical and genetic mapping of human brain cDNAs [see comments]." *Nat Genet* 2(3): 180–5.

Lunetta and Boehnke (1994). "Multipoint radiation hybrid mapping: comparison of methods, sample size requirements, and optimal study characteristics." *Genomics* 21(1): 92–103.

Priat et al. (1998). "A whole-genome radiation hybrid map of the dog genome." *Genomics* 54(3): 361–78.

Shimkets et al. (1999). "Gene expression analysis by transcript profiling coupled to a gene database query." *Nat Biotechnol* 17(8): 798–803.

Steen et al. (1999). "A high-density integrated genetic linkage and radiation hybrid map of the laboratory rat [published erratum appears in Genome Res 1999 Aug.;9(8):793]." *Genome Res* 9(6): AP1–8, insert.

Trask (1991). "Fluorescence in situ hybridization: applications in cytogenetics and gene mapping." *Trends Genet* 7(5): 149–54.

Walter et al. (1994). "A method for constructing radiation hybrid maps of whole genomes." *Nat Genet* 7(1): 22–8.

Watanabe et al. (1999). "A radiation hybrid map of the rat genome containing 5,255 markers [see comments]." *Nat Genet* 22(1): 27–36.

* cited by examiner

Primary Examiner—Kenneth R. Horlick
Assistant Examiner—Cynthia Wilder
(74) Attorney, Agent, or Firm—Ivor R. Elrifi; Mintz, Levin, Cohn, Ferris, Glovsky and Popeo, P.C.

(57) ABSTRACT

The present invention relates to methods for mapping expressed nucleic acid sequences to their chromosomal location. The invention also related to methods for mapping gene response patterns in hybrid cells containing expressed genes located on exogenous chromosomal segments.

44 Claims, 3 Drawing Sheets

TRANSCRIPTION-BASED GENE MAPPING

RELATED APPLICATIONS

This application claims priority to U.S. Provisional Application Serial No. 60/137,307 filed Jun. 3, 1999, entitled "Transcription-Based Gene Mapping", which is incorporated herein by reference in its entirety.

FIELD OF THE INVENTION

The present invention relates in general to nucleic acids an more particularly to methods for mapping expressed nucleic acid sequences to their chromosomal location, and for mapping gene response patterns.

BACKGROUND OF THE INVENTION

Mapping expressed sequences to their chromosomal locations can be an important tool in the effort to use genetics to understand the basis of disease in plants and animals, e.g., humans. Two commonly used mapping techniques are genetic mapping and physical mapping. A gene is mapped "genetically" when a polymorphism within the gene is shown to co-segregate with other polymorphisms through multiple generations. Physical mapping is performed by the demonstration of physical hybridization of a DNA probe from the gene to a chromosome (such as with fluorescent in situ hybridization), by direct DNA sequencing of a genomic region of known chromosomal location, or by the amplification of a piece of a gene from a panel of cell lines that each bear a portion of a genome of interest. See, e.g., Trask 1991 *Trends Genet.* 7: 149–154; Gyapay 1996 *Hum. Mol. Genet.* 5: 339–346; Lunetta et al., 1994 *Genomics* 21: 92–103; Priat et al., 1998 *Genomics* 54: 361–378; Steen, et al. *Genome Res. Online* (published online May 21, 1999); Watanabe, et al. 1999 *Nat. Genet.* 22: 27–36; Khan, et al. 1992 *Nat. Genet.* 2: 180–185; and Walter, et al. 1994 *Nat. Genet.* 7: 22–28.

One type of physical mapping includes performing gene-specific PCR reactions on a panel of somatic cell or radiation hybrids. These hybrids include cells having, in addition to their endogenous genome, DNA from a second species. The pattern of the presence or absence of a product can be compared to patterns of markers whose physical location is known, thus assigning a fairly accurate physical location to the gene of interest. Efforts to map large numbers of genes using radiation hybrid panels have been somewhat successful, but a large failure rate, sometimes as large as 30% or more, results from the presence of introns in genomic DNA. The introns prevent some primer pairs designed from cDNA from amplifying their target DNA. In addition, either a preliminary physical map or a large amount of genetic data is necessary to begin mapping genes using this method.

Thus, a need remains in the art for more viable method of mapping large numbers of expressed sequences to their chromosomal locations. Such methods would greatly facilitate analysis of the genetic basis for gene expression and its relationship to diseases in all types of organisms.

SUMMARY OF THE INVENTION

The present invention provides method for determining the chromosomal location of a nucleic acid sequence. Also provided are methods for identifying at least one gene whose expression is modulated by one or more exogenous genes present in a hybrid cell, and a method of mapping a network response.

This new method of mapping genes has utility beyond human genes, the majority of which will likely be mapped in the next year to two years. Canine, porcine, zebrafish, and many other genomes have neither been well-mapped, nor is there a large expressed sequence database for these organisms, yet there are valuable genetic models in these species and others which could be utilized. In these organisms and others, the application of this technique to a radiation hybrid panel, as opposed to somatic cell hybrids, could increase the number and accuracy of genes mapped.

The success of this method in identifying the map locations of expressed sequences is dependent upon the ability of the host cell to permit the proper transcription and splicing of genes from the exogenous DNA. Generally, only a fraction of genes on the exogenous DNA will be transcribed in a given cell type. "Illegitimate transcription," however, can be induced by agents such as cycloheximide and may significantly increase the fraction of genes that can be mapped in this way[11-12]. The primary difficulty in the use of this method is distinguishing between the genes expressed from the exogenous DNA and the endogenous genes that are modulated as a result of the expression of specific exogenous genes. When the complete sequence of the human genome is known, a human cell line will be the ideal vector for this protocol because the endogenous genes can be removed from the analysis by direct comparison to the human genome database. However, the identification of genes that are specifically modulated as the result of the presence of an exogenous gene or genes can potentially become a valuable functional genomics tool to build networks of gene response. The identification of which exogenous gene(s) lead to activation of endogenous gene(s) of interest through a systematic method of analyzing a large number of genetic combinations for differential gene expression may lead to a better understanding of genetic interactions. Thus, the "noise" in this mapping experiment may help decode patterns of gene response on a genome-wide scale.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 is a graphic representation of the magnitude of difference in gene fragment abundance between nucleic acids found to be increased (right of center) or decreased (left of center) in two hybrid cell lines relative to parental cell line controls. The graphs are plotted according to the fold difference. The differences in the chromosome 22 hybrid (top), FIG. 1A and chromosome 1 hybrid (bottom), FIG. 1B relative to the control are shown.

FIG. 2 is a graphic depiction of a nucleic acid transcript profile. The gene fragments specific to the *Homo sapiens* chromosome 22-containing A9 hybrid cells (top panel labeled A9+HS22), FIG. 2A compared to the normal mouse line (bottom panel labeled A9 only), FIG. 2B are denoted by a vertical line. Complementary DNA (cDNA) from three separate cultures of each cell line underwent three separate transcript profile reactions, which were averaged for each of the three samples. The composite for each of the three samples is represented by the black, dark gray and light gray lines in the chromatogram.

FIG. 3 illustrates oligonucleotide poisoning of specific gene fragments to confirm fragment sequence identity. In each chromatogram the dark gray trace represents the transcript profile after reamplification of the original transcript profile reaction. The light gray trace represents that same reaction in the presence of a sequence-specific oligonucleotide synthesized from DNA sequence from GenBank from ATP synthase (top), FIG. 3A or TIMP-3 (bottom), FIG. 3B.

DETAILED DESCRIPTION OF THE INVENTION

The invention provides methods for mapping chromosomal genes by detecting genes expressed in hybrids that are not expressed in non-hybrid control cells to rapidly create a database of expressed genes from a given chromosomal location. The invention utilizes hybrid panels but does not require the gene-specific amplification process to rapidly map known and novel genes.

This methods of the invention can be used to map genes in any organism of interest, e.g., canine, porcine, zebrafish, mouse, rat, Drosophila, spp. The method is suited for genomes that have either not been well-mapped or do not have a large expressed sequence database for these organisms. Thus, any organism that is a valuable genetic model for a particular disease, both human and non-human diseases, could be utilized. In these organisms and others, the application of the instant invention to a radiation hybrid (RH) panel, as opposed to somatic cell hybrids, can increase the number and accuracy of genes mapped. Detailed description of RH mapping may be found in, e.g., Cox et al. (1990) *Science* 250: 245–250; Boehnke et al. (1991) *Am J Hum Genet* 49: 1174–1188; and Walter et al. (1994) *Nat Genet* 7: 22–28.

The output of a systematic comparison between hybrid cell lines and the non-hybrid host cell line is the generation of a database of chromosome-specific expressed gene fragments. Such a database has utility not only in the mapping of some genes, but in future work in which a differential gene expression profile in, for example, a disease model compared to a normal control, can be compared to the mapped fragment database to instantly assign chromosomal location. The same oligonucleotide used to confirm the gene identity of the gene fragment in the disease model can be used in the appropriate mapping panel member.

In one aspect, the invention provides a method of determining the chromosomal location of an expressed nucleic acid sequence. First, a nucleic acid from one or more hybrid cell lines, e.g., a somatic hybrid cell line or a radiation hybrid panel, is obtained. As used herein, cell hybrids include cells from two distinct organisms, preferably organisms from different species. The cell hybrids include genomes from at least two different organisms, one of whose genome is referred to herein as an endogenous genome, and the other as the exogenous genome. Typically, the endogenous genome is one that is more completely represented in the hybrid cell, and the exogenous genome is one that is less completely represented in the hybrid cell. Examples of endogenous and exogenous genomes include mouse and human genomes, respectively for an A9 mouse cell line containing a single human chromosome, e.g., chromosome 1 or chromosome 22. See, e.g., FIG. 1 and Example 1, below.

Cell hybrids, e.g., somatic cell hybrids, thus can include non-human cell lines previously fused with a human cell. In somatic cell hybrids, human chromosomes are typically lost during subsequent cell divisions until one or a few human chromosomes remain as exogenous chromosomes. The endogenous chromosomes of the non-human host cell remain.

In the method, the RNA level of one or more transcripts in the hybrid cell lines is compared to the level of the transcripts in a reference cell. RNA levels between the cell types can be compared using any method known in the art. In preferred embodiments, the RNA levels are compared using methods described in U.S. Pat. No. 5,871,697. In these methods, RNA molecules are isolated from the somatic cell hybrid and cDNA is prepared. The cDNA is then probed with one or more enzymes, e.g., probing by digesting the cDNA with restriction enzymes. When multiple enzymes are used, it is preferred that each enzyme recognizes a different target subsequence.

One or more output signals are then generated from the sample after probing. Preferably each output signal is produced from a nucleic acid in the sample by recognition of one or more target nucleotide subsequences in the nucleic acid by said enzyme. The output signal preferably includes a representation of (i) the length between occurrences of target nucleotide subsequences in the nucleic acid, and (ii) the identities of the target nucleotide subsequences in the nucleic acid or the identities of the sets of target nucleotide subsequences among which are included the target nucleotide subsequences in the nucleic acid.

The output signals from the first hybrid cell sample is then compared with the output signals of a second sample that is processed analogously. The second sample is preferably obtained from a reference cell. The reference cell typically includes the endogenous genome of the hybrid cell but does not include the exogenous genome present in the hybrid cell.

A nucleic acid present at increased levels in the first hybrid cell relative to the reference cell indicates that the nucleic acid is encoded by a gene present in the exogenous genome present in the first hybrid cell. Associating increased transcription in a hybrid cell containing a known exogenous genome indicates the transcribed sequence is derived from the exogenous genome.

In some embodiments, the method further includes searching a nucleotide sequence database to determine sequences that are predicted to produce, or to identify the absence of any sequences that are predicted to produce, one or more output signals produced by the nucleic acid. The database can include a plurality of known nucleotide sequences of nucleic acids that may be present in the sample.

A sequence from the database is predicted to produce the one or more output signals when the sequence from the database has both (i) the same length between occurrences of target nucleotide subsequences as is represented by the one or more output signals, and (ii) the same target nucleotide subsequences as are represented by the one or more output signals, or target nucleotide subsequences that are members of the same sets of target nucleotide subsequences represented by the one or more output signals. A predicted sequence that corresponds to one or more output signals within any sample indicates the identity of the nucleic acid represented by the signal.

Preferably, several databases are searched. Preferably, one or more of the databases represents the nucleotide sequences of the endogenous and exogenous genomes that comprise the hybrid cell, thereby identifying a genomic origin of the identified signals.

In some embodiments, the method further includes providing a third nucleic acid sample from a second hybrid cell, the third sample being processed as the earlier samples. The second hybrid cell includes the endogenous genome present in the first hybrid cell and an exogenous genome distinct from the exogenous genome present in the first hybrid cell. Next, the output signals from the third sample is compared with the output signals of the first sample and the second sample. A nucleic acid present in increased levels in the first hybrid cell and the second hybrid cell relative to the reference cell indicates that the nucleic acid is a host-cell specific nucleic acid encoded by an endogenous gene responsive to the presence of the exogenous genome. If desired, one or more nucleotide sequence databases can be searched to determine sequences that are predicted to produce or the absence of any sequences that are predicted to produce the one or more output signals produced by the nucleic acid in the third sample. The database can include, e.g., a plurality of known nucleotide sequences of nucleic acids that may be present in the sample, a sequence from the database being predicted to produce the one or more output signals. The sequence from the database preferably has both (i) the same length between occurrences of target nucleotide subsequences as is represented by the one or more output signals, and (ii) the same target nucleotide subsequences as are represented by the one or more output signals, or target nucleotide subsequences that are members of the same sets of target nucleotide subsequences represented by the one or more output signals. A predicted sequence that corresponds to one or more output signals within any sample indicates the identity of the nucleic acid represented by the signal. When multiple databases are searched, each may optionally represent the nucleotide sequences of the endogenous and exogenous genomes that comprise the hybrid cell, thereby identifying a genomic origin of the identified signals.

The hybrid cell can be, e.g., a somatic cell hybrid, such as a radiation hybrid panel cell line-derived cell. Alternatively, or in addition, a hybrid cell is a fusion product of a human cell and a non-human cell. In addition, the hybrid cells can include cells derived from a model organism for studying a disease. For example, the cells may contain a chromosomal segment known or suspected of containing gene causing a disease.

In general, any source of DNA can serve as the exogenous chromosome. In some embodiments, the exogenous chromosomal segment in the hybrid cell is a human cell, and the reference cell is a non-human cell. In other embodiments, the exogenous chromosomal segment is non-human, and the reference cell is human. The exogenous genome can also be, e.g. an artificial chromosome (such as a yeast artificial chromosomes). The exogenous genome can be either a complete or other-than-full length chromosome, e.g., a partial chromosome or duplicated (in whole or in part) chromosome.

In some embodiments, the first nucleic acid sample is derived from the region selected from the 5' end, the 3' end and/or the interior region of an RNA molecule.

The reference sample of the invention may be derived from expressed sequence tags (ESTs), sequence-tagged sites (STSs) or a previously derived signal output database.

In some aspects, the method further includes ligating adapter oligonucleotides to the termini of digested cDNA molecules produced by restriction digestion. The ligation products are optionally amplified by PCR, after which the amplified PCR products may be separated by gel electrophoresis.

To verify the identity of an identified sequence, oligonucleotide poisoning may be used as described in WO 99/07896, which is incorporated herein by reference in its entirety. In oligonucleotide poisoning, restriction fragments which map in end sequence and length to known rat genes are used as templates for the design of unlabeled oligonucleotide primers. An unlabeled oligonucleotide designed against one end of the restriction fragment was added in excess to the original reaction, which was then re-amplified for an additional 10 cycles. This reaction was then electrophoresed and compared to a control reaction reamplified without the unlabeled oligonucleotide to evaluate the selective diminution of the peak of interest. A loss or diminution of a given band confirms that the given sequence contains at least a portion of the determining sequence used to design the unlabeled "poisoning" oligonucleotide.

The invention also provides a method for a identifying a gene whose expression is modulated by at least one gene located on exogenous DNA present in a hybrid cell. First, a nucleic acid from one or more hybrid cell lines, e.g., a somatic hybrid cell line or a radiation hybrid panel, is obtained. As used herein, cell hybrids include cells from two distinct organisms, preferably organisms from different species. The cell hybrids include genomes from at least two different organisms, one of whose genome is referred to herein as an endogenous genome, and the other as the exogenous genome. Typically, the endogenous genome is one that is more completely represented in the hybrid cell, and the exogenous genome is one that is less completely represented in the hybrid cell. Examples of endogenous and exogenous genomes include mouse and human genomes, respectively for an A9 mouse cell line containing a single human chromosome, e.g., chromosome 1 or chromosome 22. See, e.g., FIG. 1 and Examples 1 and 2, below.

Cell hybrids, e.g., somatic cell hybrids, thus can include non-human cell lines previously fused with a human cell. In somatic cell hybrids, human chromosomes are typically lost during subsequent cell divisions until one or a few human chromosomes remain as exogenous chromosomes. The endogenous chromosomes of the non-human host cell remain.

In the method, the RNA level of one or more transcripts in the hybrid cell lines is compared to the level of the transcripts in a reference cell. RNA levels between the cell types can be compared using any method known in the art. In preferred embodiments, the RNA levels are compared using methods described in U.S. Pat. No. 5,871,697. In these methods, RNA molecules are isolated from the somatic cell hybrid and cDNA is prepared. The cDNA is then probed with one or more enzymes, e.g., probing by digesting the cDNA with restriction enzymes. When multiple enzymes are used, it is preferred that each enzyme recognizes a different target subsequence.

One or more output signals are then generated from the sample after probing. Preferably each output signal is produced from a nucleic acid in the sample by recognition of one or more target nucleotide subsequences in the nucleic acid by said enzyme. The output signal preferably includes a representation of (i) the length between occurrences of target nucleotide subsequences in the nucleic acid, and (ii) the identities of the target nucleotide subsequences in the nucleic acid or the identities of the sets of target nucleotide subsequences among which are included the target nucleotide subsequences in the nucleic acid.

The output signals from the first hybrid cell sample is then compared with the output signals of a second sample that is processed analogously. The second sample is preferably obtained from a reference cell. The reference cell typically includes the endogenous genome of the hybrid cell but does not include the exogenous genome present in the hybrid cell. A third nucleic acid sample is provided from a second hybrid cell, the third sample being processed as the earlier samples. The second hybrid cell includes the endogenous genome present in the first hybrid cell and an exogenous genome distinct from the exogenous genome present in the first hybrid cell. Next, output signals from the third sample is compared with the output signals of the first sample and the second sample. A nucleic acid present at increased levels in the first hybrid cell relative to the reference cell indicates that the nucleic acid is encoded by a gene present in the exogenous genome present in the first hybrid cell. The host cell-specific nucleic acids responsive to the exogenous chromosomal segment contained within the first cell is indicated as being modulated by at least one gene located on the portion of the exogenous genome within the hybrid cell.

The following examples illustrate particular non-limiting embodiments of the invention.

EXAMPLES

Example 1
Mapping Genes Using Expression Analysis

Differential gene expression (DGE) techniques are described in U.S. Pat. No. 5,871,697 and in U.S. provisional application serial No. 09/417,386 filed Oct. 13, 1999, both of which are incorporated by reference herein in their entirety, and which are referred to as GeneCalling and SeqCalling, respectively. These DGE techniques were used to analyze expressed genes in somatic hybrid cell lines compared to non-hybrid parental cell line. DGE was performed on a mouse-human hybrid bearing the intact human chromosome 1 (A9+HS 1), a mouse-human hybrid bearing intact human chromosome 22 (A9+HS 22), and the parental A9 normal mouse cell line from which these hybrids were generated. See, e.g., Cuthbert, et al. 1995 Cytogenet. Cell Genet. 71: 68–76. Gene expression profiles were generated by isolating and purifying polyadenylated mRNA, converting it to double-stranded complementary DNA (cDNA), digesting the cDNA with pairs of restriction enzymes, purifying and electrophoresing the reactions as reported previously. See, e.g., Shimkets et al. 1999 Nat. Biotech. 17: 798–803.

Gene fragments appearing at elevated levels or de novo in the hybrids relative to the normal mouse cell line can either be human genes transcribed in the mouse from the foreign chromosome, or mouse genes induced by the presence of the foreign DNA. By removing those gene fragments from the analysis that are detected as differences in multiple hybrids bearing different human chromosomes, many mouse response genes can be removed, leaving primarily the human genes expressed in the mouse. Using the sequence information from the ends of the restriction fragments, their lengths, and reference nucleic acids from databases of known genes expressed in mouse and human, the most likely gene, whether mouse or human, can be assigned for each band on the basis of how many bands were detected for a given gene in the database relative to how many were predicted given a synthetic restriction digest of that database.

Figure 1A:
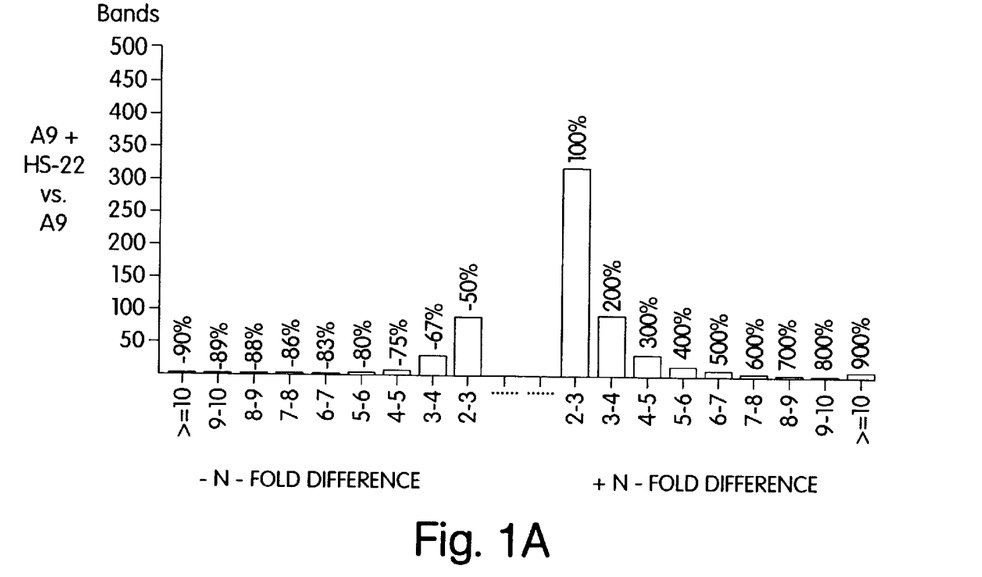
Figure 1B:
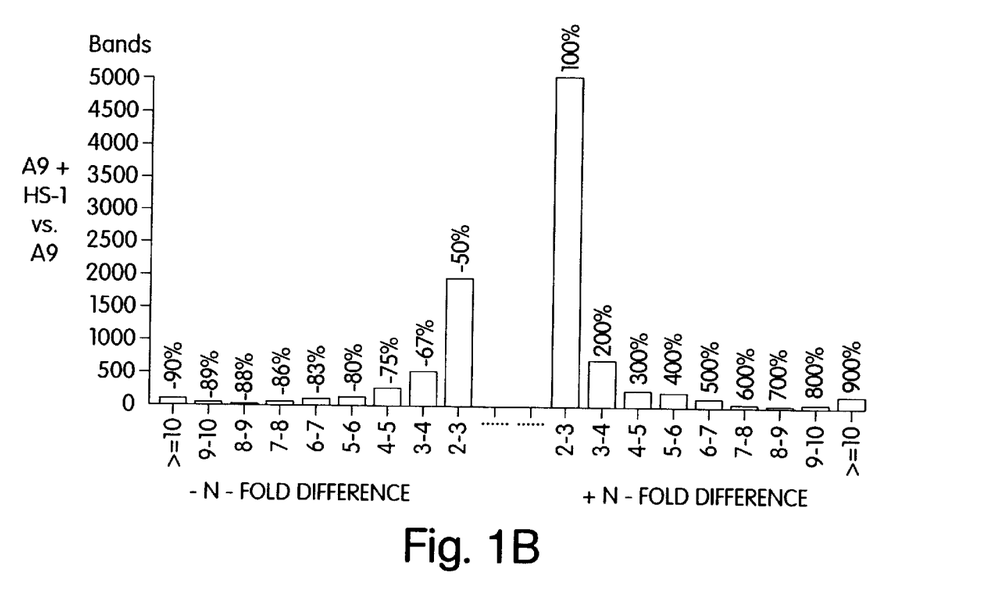
Figure 2A:
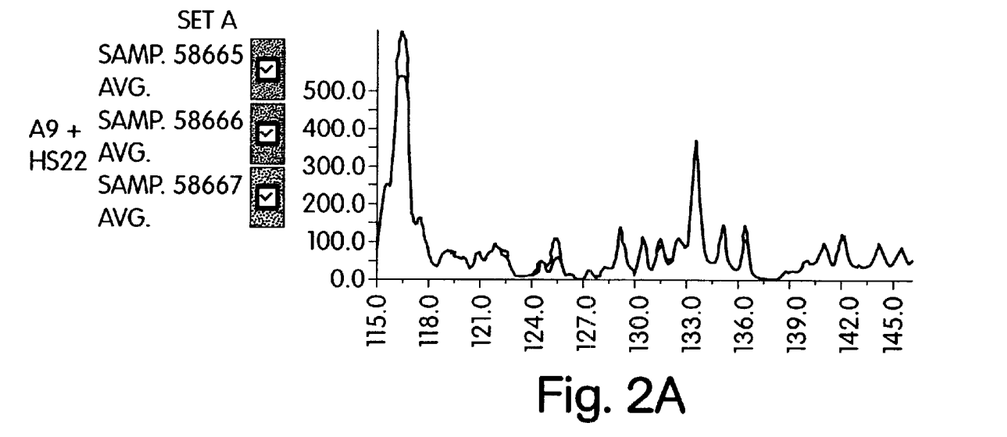
Figure 2B:
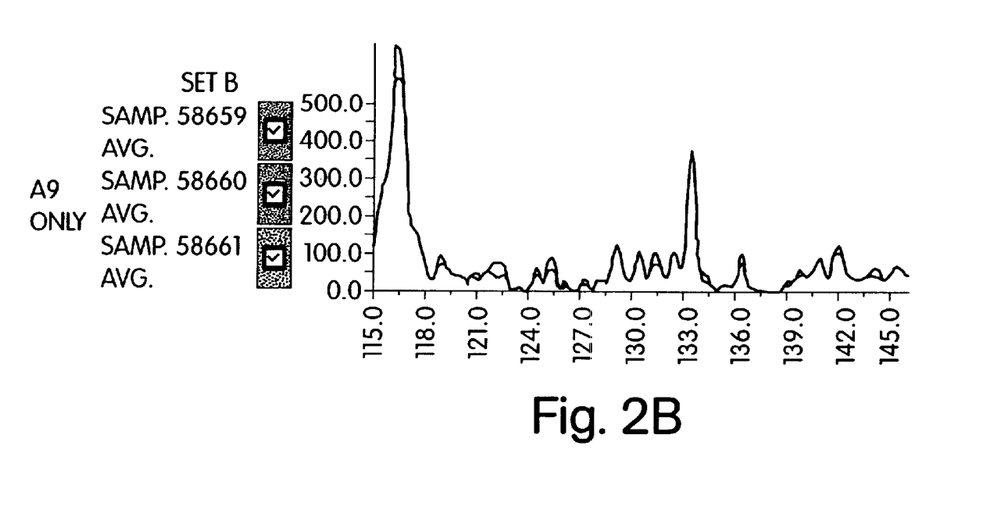

In generating the expression profiles of the three cell lines used, 100 restriction enzyme pairs were used to digest, in separate reactions in triplicate, the cDNA populations prepared from three separate cultures of each cell line. Approximately 24,000 gene fragments were generated and measured for each sample. In the comparison of the human chromosome 1-containing hybrid cell line to the normal mouse line, 2668 differences were found (Table 1), the majority of which represented genes at higher levels in the hybrid (FIG. 1). When the human chromosome 22-containing hybrid cell line was compared to the normal mouse line, only 638 differences were found, most likely due to the fact that human chromosome 22 is significantly smaller and therefore contains significantly fewer genes that human chromosome 1 (Table 1). In both of these comparisons, the hybrid possesses more peaks or more abundant peaks than the control cell line (FIG. 2). While the magnitude of the differences are not always measured as de novo (i.e. from baseline), this is most likely the result of background from other gene fragments migrating at nearby or identical positions. Across both comparisons, there were 90 gene fragments at higher levels in each hybrid and 73 fragments at lower levels, most likely corresponding to mouse genes that were either induced or suppressed as a result of the presence of the foreign DNA.

TABLE 1

| Comparison | # Fragments Assayed | # Significant Differences | % Differences |
| --- | --- | --- | --- |
| Mouse + HS22 vs. Mouse | 24,000 | 638 | 2.7% |
| Mouse + HS1 vs Mouse | 24,000 | 2668 | 9.5% |

Figure 3A:
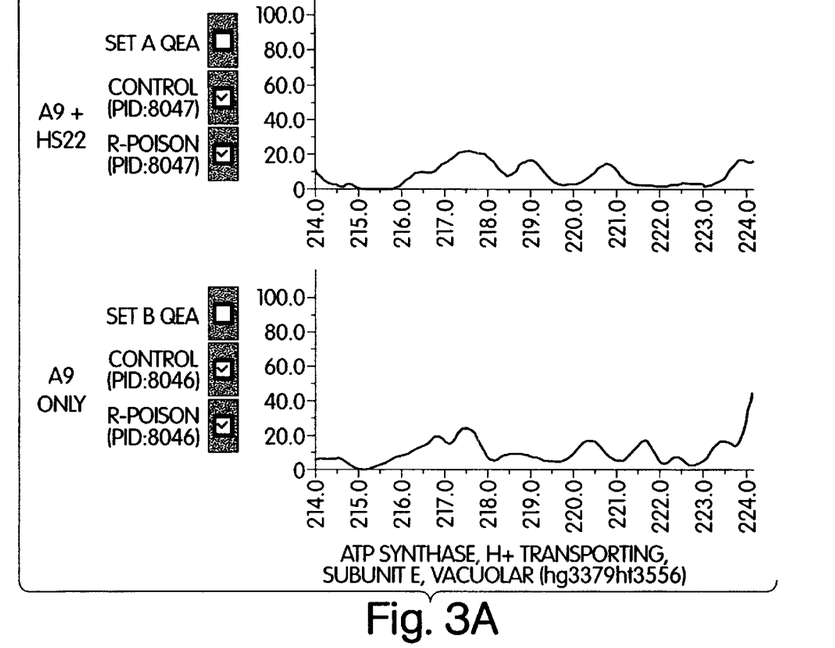
Figure 3B:
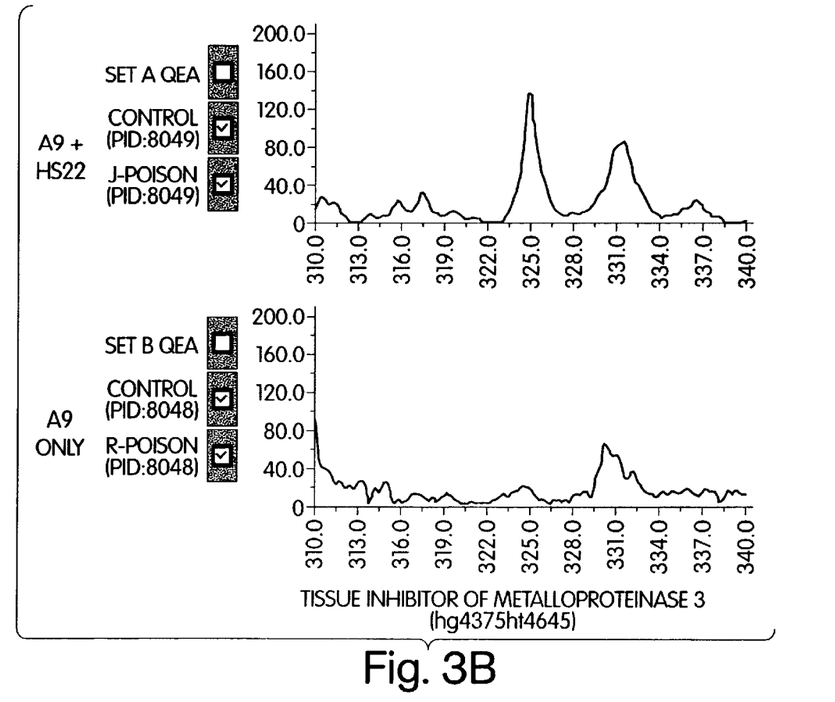

In order to determine what fraction of genes whose map locations were known could be detected using this method, the chromosome 22 hybrid data was compared to the list of expressed human genes known to reside on human 22, as provided by the U.S. National Library of Medicine web site entitled Online Mendelian Inheritance in Man (OMIM). At least 1 fragment from 35 of the 75 expressed sequences in this database was detected in this comparison. The identity of the gene fragments was confirmed using oligonucleotide poisoning, a competitive PCR methodology in which an excess of unlabeled oligonucleotide made from sequence of the human gene predicted to correspond to the fragment of interest is added to the original DGE reaction and subjected to an additional 10 cycles of PCR. The excess of unlabeled oligonucleotide results in the specific disappearance of the gene fragment primed by the gene-specific oligonucleotide (FIG. 3). The oligonucleotide poisoning methodology is described more completely in PCT Publication WO 99/07896, which is incorporated herein by reference in its entirety.

The output of a systematic comparison between hybrid cell lines and the non-hybrid host cell line is the generation of a database of chromosome-specific expressed gene fragments. Such a database has utility not only in the mapping of some genes, but in future work in which a differential gene expression profile in, for example, a disease model compared to a normal control, can be compared to the mapped fragment database to instantly assign chromosomal location. The same oligonucleotide used to confirm the gene identity of the gene fragment in the disease model can be used in the appropriate mapping panel member.

Cell culture. Three cell lines, namely normal mouse A9 cells (ATCC GM00346B) and A9 hybrids bearing human chromosomes 1 (ATCC GM13258) or 22 (ATCC 13139A) were grown to confluency in identical media according to American Type Culture Collection (ATCC) protocol provided with the cell lines. Approximately $10^7$ cells were harvested by the addition of Trizol (BRL, Grand Island N.Y.).

GeneCalling DGE chemistry. Total cellular RNA was isolated with Trizol using one-tenth volume of bromochloropropane for phase separation (Molecular Research Center Inc., Cincinnati Ohio). Contaminating DNA was removed by treatment with DNase I (Promega, Madison Wis.) in the presence of 0.01 M DTT (BRL, Grand Island N.Y.) and 1 unit/$\mu$l RNasin (Promega, Madison Wis.). Following phenol/chloroform extraction, RNA quality was evaluated by spectrophotometry and formaldehyde agarose gel electrophoresis, and RNA yield was estimated by fluorometry with OliGreen (Molecular Probes, Eugene Oreg.). Poly(A)$^+$ RNA was prepared from 100 $\mu$g total RNA using oligo(dT) magnetic beads (PerSeptive, Cambridge Mass.), and quantitated with fluorometry.

First strand cDNA was prepared from 1.0 $\mu$g of poly(A)$^+$ RNA with 200 pmols oligo(dT)$_{25}$V (wherein V=A, C or G) using 400 units of Superscript II reverse transcriptase (BRL, Grand Island N.Y.). Second strand synthesis was performed at 16° C. for 2 h following the addition of 10 units of $E.\ coli$ DNA ligase, 40 units of $E.\ coli$ DNA polymerase, and 3.5 units of $E.\ coli$ RNase H (all from BRL, Grand Island N.Y.). Five units of T4 DNA polymerase was then added, and incubation at 16° C. was continued for 5 minutes. The reaction was then treated with 5 units of arctic shrimp alkaline phosphatase (USB, Cleveland Ohio) at 37° C. for 30 minutes, and cDNA purified by phenol/chloroform extraction. The yield of cDNA was estimated using fluorometry with PicoGreen (Molecular Probes, Eugene Oreg.).

cDNA fragmentation, tagging and amplification were performed in a 3-step process. Fragmentation was achieved by restriction enzyme digestions in a 50 $\mu$l reaction mix containing 5 units of each restriction enzyme, 1 ng of double-stranded cDNA and 5 $\mu$l of the appropriate 10× buffer restriction endonuclease buffer. Coverage of most mRNAs was achieved by performing 80 separate sets of cDNA fragmentation reactions, each with a different pair of restriction enzymes. Tagging was achieved by ligation of amplification cassettes with ends compatible to the 5' and 3' ends of the cDNA fragments. Incubation of the ligation was performed at 16° C. for 1 hour in 10 mM ATP, 2.5% PEG, 10 units T4 DNA ligase and 1× ligase buffer. Amplification was achieved by the addition of the following reagents: 2 $\mu$l 10 mM dNTP, 5 $\mu$l 10× TB buffer (500 mM Tris, 160 mM $(NH_4)_2SO_4$, 20 mM $MgCl_2$, pH 9.15), 0.25 $\mu$l Klentaq (Clontech Advantage): PFU (Stratagene, La Jolla Calif.) (16:1), 32.75 $\mu$l $H_2O$. Twenty (20) cycles of amplification (one cycle being 30 seconds at 96° C., 1 minute at 57° C., 2 minutes at 72° C.) were followed by 10 minutes at 72° C. PCR product purification was performed using MPG streptavidin beads (CPG). After washing the beads twice with buffer 1 (3 M NaCl, 10 mM TRIS-HCl, 1 mM EDTA, pH 7.5), 20 $\mu$l of buffer 1 was mixed with the PCR product for 10 minutes at room temperature, separated with a magnet, and washed once with buffer 2 (10 mM TRIS, 1 mM EDTA, pH 8.0). The beads were then dried and resuspended in 3 $\mu$l of buffer 3 (80% (v/v) formamide, 4 mM EDTA, 5% TAMRA- or ROX-tagged molecular size standard (PE-Applied Biosystems, Foster City Calif.). Following denaturation (96° C. for 3 minutes), samples were loaded onto 5% polyacrylamide, 6M urea, 0.5× TBE ultrathin gels and electrophoresed on a Niagara instrument. The Niagara gel electrophoresis methodology is described in U.S. Pat. No. 5,938,904 and in PCT Publication WO 96/35810, both of which are incorporated herein by reference in their entirety. PCR products were visualized utilizing the fluorescent FAM label at the 5' end of one of the PCR primers. This process ensures that all detected fragments have been digested by both enzymes, because only those nucleic acids that are tagged with ROX are bound on beads and only those FAM labeled ROX-tagged products are detected by the fluorescence-mediated visualization.

The primary components of the Niagara gel electrophoresis system are an interchangeable horizontal ultrathin gel cassette mounted in a platform employing stationary laser excitation and a multi-color CCD imaging system. Each gel cassette is loaded in 4 cycles of 12 wide (48 lanes total) directly from a 96-well plate using a robotic arm. The Niagara system has the advantage of high throughput, with separation of fragments between 30 and 450 bases in 45 minutes.

Gel interpretation. The output of the electrophoresis instruments were processed using the Java-based Internet-ready Open Genome Initiative (OGI) software suite. Gels images were first visually checked and tracked. Each lane contained the FAM-labeled products of a single GeneCalling DGE reaction plus a sizing ladder spanning the range from 50 to 500 bp. The ladder peaks provide a correlation between camera frames (collected at 1 Hz) and DNA fragment size in base pairs. After tracking, lanes were extracted and the peaks in the sizing ladder were found. Linear interpolation between the ladder peaks was used to convert the fluorescence traces from frames to base pairs. A final quality control step checked for low signal-to-noise, poor peak resolution, missing ladder peaks, and lane-to-lane bleed. Data that passed all of these criteria were submitted as point-by-point length versus amplitude addresses to an Oracle 8 database.

Difference identification. For each restriction enzyme pair (sub-sequence) in each sample set, a composite trace was calculated compiling all the individual sample replicates followed by application of a scaling algorithm for best fit in order to normalize the traces of the experimental set versus that of the control. The scaled traces were then compared on a point-by-point basis to define areas of amplitude difference which met the minimum pre-specified threshold for a significant difference. Once a region of difference was identified, the local maximum for the corresponding traces of each set was then identified. The variance of the difference was determined by $$\sigma_\Delta^2(j) = \lambda_1(j)^2 \sigma_{Total}^2(j:S_1) + \lambda_2(j)^2 \sigma_{Total}^2(j:S_2)$$

where $\lambda_1(j)$ and $\lambda_2(j)$ represent scaling factors and (j:S) represents the trace composite values over multiple samples. The probability that the difference is statistically significant was calculated by $$P(j) = 1 - \int_{-\Delta}^{\Delta} dy \frac{1}{\sqrt{2\pi\sigma_\Delta^2}} \exp\left(\frac{-y^2}{2\sigma_\Delta^2}\right).$$

where y is the relative intensity. All difference peaks were stored as unique database addresses in the specified expression difference analysis.

Equivalents

From the foregoing detailed description of the specific embodiments of the invention, it should be apparent that unique method for transcription based gene mapping and gene expression profiling have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For instance, the choice of hybrid cells, host cell types, or exogenous chromosome segments is believed to be a matter of routine for a person of ordinary skill in the art with knowledge of the embodiments described herein.

What is claimed is:

1. A method of determining the chromosomal location of an expressed nucleic acid sequence, the method comprising:
   a) providing a first nucleic acid sample from a hybrid cell, wherein the hybrid cell includes an endogenous genome and at least a portion of an exogenous genome, wherein the first nucleic acid sample is a cDNA population derived from a population of RNA molecules isolated from said hybrid cell;
   b) probing said sample with one or more endonuclease enzymes, wherein each of said enzymes recognize a different target nucleotide subsequence or a different set of target nucleotide subsequences;
   c) generating one or more output signals from said sample probed by said enzyme, each output signal being produced from a nucleic acid in said sample by recognition of one or more target nucleotide subsequences in said nucleic acid by said enzyme and comprising a representation of (i) the length between occurrences of target nucleotide subsequences in said nucleic acid, and (ii) the identities of said target nucleotide subsequences in said nucleic acid or the identities of said sets of target nucleotide subsequences among which are included the target nucleotide subsequences in said nucleic acid, and measuring the level of said one or more output signals; and
   d) comparing the output signals from said hybrid cell sample with the output signals of a second sample that is processed as in steps (b) and (c), wherein the second sample is obtained from a reference cell, wherein said reference cell comprises the endogenous genome of said hybrid cell but does not include the exogenous genome present in said hybrid cell;
whereby a nucleic acid present at increased levels in the hybrid cell relative to the reference cell indicates that said nucleic acid is encoded by a gene present in the exogenous genome present in said hybrid cell, thereby determining the chromosomal location of an expressed nucleic acid sequence.

2. The method of claim 1, wherein the method further comprises searching a nucleotide sequence database to determine sequences that are predicted to produce or the absence of any sequences that are predicted to produce said one or more output signals produced by said nucleic acid, said database comprising a plurality of known nucleotide sequences of nucleic acids that may be present in the sample, a sequence from said database being predicted to produce said one or more output signals when the sequence from said database has both (i) the same length between occurrences of target nucleotide subsequences as is represented by said one or more output signals, and (ii) the same target nucleotide subsequences as are represented by said one or more output signals, or target nucleotide subsequences that are members of the same sets of target nucleotide subsequences represented by said one or more output signals, wherein a predicted sequence that corresponds to one or more output signals within any sample indicates the identity of the nucleic acid represented by said signal.

3. The method of claim 2, wherein several databases are searched, each database representing the nucleotide sequences of the endogenous and exogenous genomes that comprise the hybrid cell, thereby identifying a genomic origin of the identified signals.

4. The method of claim 1, wherein the method further comprises:
   e) providing a third nucleic acid sample from a second hybrid cell, said third sample being processed as in steps (b) and (c), wherein said second hybrid cell comprises the endogenous genome present in said hybrid cell from claim 1 and an exogenous genome distinct from the exogenous genome present in said hybrid cell from claim 1; and
   f) comparing the output signals from said third sample with the output signals of the first sample and the second sample;
whereby a nucleic acid present in increased levels in the hybrid cell from claim 1 and the second hybrid cell relative to the reference cell indicates that said nucleic acid is a host-cell specific nucleic acid encoded by an endogenous gene responsive to the presence of the exogenous genome.

5. The method of claim 4, wherein the method further comprises searching a nucleotide sequence database to determine sequences that are predicted to produce or the absence of any sequences that are predicted to produce said one or more output signals produced by said nucleic acid, said database comprising a plurality of known nucleotide sequences of nucleic acids that may be present in the sample, a sequence from said database being predicted to produce said one or more output signals when the sequence from said database has both (i) the same length between occurrences of target nucleotide subsequences as is represented by said one or more output signals, and (ii) the same target nucleotide subsequences as are represented by said one or more output signals, or target nucleotide subsequences that are members of the same sets of target nucleotide subsequences represented by said one or more output signals, wherein a predicted sequence that corresponds to one or more output signals within any sample indicates the identity of the nucleic acid represented by said signal.

6. The method of claim 5, wherein several databases are searched, each database representing the nucleotide sequences of the endogenous and exogenous genomes that comprise the hybrid cell, thereby identifying a genomic origin of the identified signals.

7. The method of claim 1, wherein a hybrid cell is chosen from the group consisting of a somatic cell hybrid and a radiation hybrid panel cell line-derived cell.

8. The method of claim 1, wherein said hybrid cell is a fusion product of a human cell and a non-human cell.

9. The method of claim 1, wherein the cells are derived from a model organism for studying a disease.

10. The method of claim 9, wherein the disease is caused by a gene located on an exogenous chromosomal segment of the hybrid cell.

11. The method of claim 1, wherein the endogenous genome is a human genome.

12. The method of claim 1, wherein the endogenous genome is a non-human genome.

13. The method of claim 10, wherein the exogenous chromosomal segment is human.

14. The method of claim 1, wherein the portion of the exogenous genome is non-human.

15. The method of claim 1, wherein the portion of the exogenous genome is an artificial chromosome.

16. The method of claim 15, wherein the portion of the exogenous genome is a yeast artificial chromosome.

17. The method of claim 1, wherein the portion of the exogenous genome is a complete chromosome.

18. The method of claim 1, wherein the portion of the exogenous genome is a partial chromosome segment.

19. The method of claim 1, wherein the cDNA population is derived from the region selected from the 5' end, the 3' end and the interior region of the RNA molecule.

20. The method of claim 1, wherein the cDNA population is derived from expressed sequence tags (ESTs).

21. The method of claim 1, wherein the nucleic acid sample is derived from sequence-tagged sites (STSs).

22. The method of claim 1, wherein the reference cell signal output is a database.

23. The method of claim 1, wherein the enzyme is a restriction enzyme.

24. The method of claim 23, wherein the sample is comprised of a complementary DNA (cDNA) molecule and the restriction enzyme digests the cDNA molecule at the target nucleotide subsequences contained therein.

25. The method of claim 24, further comprising ligating adapter oligonucleotides to the termini of the digested cDNA molecules.

26. The method of claim 25, further comprising amplifying the ligation products.

27. The method of claim 24, further comprising separating the amplified products.

28. The method of claim 27, wherein said separating is by gel electrophoresis.

29. The method of claim 1, further comprising confirming the identity of gene with the oligonucleotide poisoning technique.

30. The method of claim 2, further comprising confirming the identity of gene with the oligonucleotide poisoning technique.

31. The method of claim 4, further comprising confirming the identity of gene with the oligonucleotide poisoning technique.

32. The method of claim 5, further comprising confirming the identity of gene with the oligonucleotide poisoning technique.

33. The method of claim 1, further comprising inducing illegitimate transcription of genes in the hybrid and reference cells prior to providing the populations of nucleic acids from the cells.

34. The method of claim 33, wherein the inducing is provided via drug treatment of the host cell.

35. The method of claim 34, wherein the drug is cycloheximide.

36. The method of claim 4, further comprising inducing illegitimate transcription of genes in the hybrid and reference cells prior to providing the populations of nucleic acids from the cells.

37. The method of claim 36, wherein the inducing is provided via drug treatment of the host cell.

38. The method of claim 37, wherein the drug is cycloheximide.

39. A method of detecting at least one gene whose expression is modulated by at least one gene located on exogenous DNA within a hybrid cell, the method comprising:
   a) providing a first nucleic acid sample from a first hybrid cell, wherein the first hybrid cell comprises an endogenous genome and at least a portion of an exogenous genome, wherein the first nucleic acid sample is a cDNA population derived from a population of RNA molecules isolated from said first hybrid cell;
   b) probing said sample with one or more endonuclease enzymes, wherein each of said enzymes recognizes a different target nucleotide subsequence or a different set of target nucleotide subsequences;
   c) generating one or more output signals from said sample probed by said enzyme, each output signal being produced from a nucleic acid in said sample by recognition of one or more target nucleotide subsequences in said nucleic acid by said enzyme and comprising a representation of (i) the length between occurrences of target nucleotide subsequences in said nucleic acid, and (ii) the identities of said target nucleotide subsequences in said nucleic acid or the identities of said sets of target nucleotide subsequences among which are included the target nucleotide subsequences in said nucleic acid, and measuring the level of said one or more output signals;
   d) comparing the output signals from said first hybrid cell sample with the output signals of a second sample that is processed as in steps (b) and (c), wherein the second sample is obtained from a reference cell, wherein said reference cell comprises the endogenous genome of said hybrid cell but does not include the exogenous genome present in said hybrid cell; whereby a nucleic acid present at increased levels in the first hybrid cell relative to the reference cell indicates that said nucleic acid is encoded by a gene present in the exogenous genome present in said first hybrid cell;
   e) providing a third nucleic acid sample from a second hybrid cell, said third sample being processed as in steps (b) and (c), wherein said second hybrid cell comprises the endogenous genome present in said first hybrid cell and an exogenous genome distinct from the exogenous genome present in said first hybrid cell; and
   f) comparing the output signals from said third sample with the output signals of the first sample and the second sample, whereby a nucleic acid present in increased levels in the first hybrid cell and the second hybrid cell relative to the reference cell indicates that said nucleic acid is a host-cell specific nucleic acid encoded by an endogenous gene, wherein expression of said endogenous gene is responsive to the presence of at least one gene product encoded by the exogenous genome;

whereby the host cell-specific nucleic acids responsive to the exogenous chromosomal segment contained within the first cell is indicated as being modulated by at least one gene located on the portion of the exogenous genome within the hybrid cell, thereby detecting a gene whose expression is modulated by at least one gene located on exogenous DNA within a hybrid cell.

40. The method of claim 39, wherein the population of nucleic acids is derived from at least one cell from a model organism used for studying a disease.

41. The method of claim 40, wherein the disease is a human disease.

42. A method of mapping networks of gene response; the method comprising:
   a) identifying host-cell specific nucleic acids responsive to at least one gene located on an exogenous chromosomal segment according to claim 39; and
   b) determining which host-cell specific nucleic acids is responsive to which gene;

thereby mapping the network of genes responsive to any one gene located on the portion of the exogenous genome.

43. The method of claim 42, wherein the population of nucleic acids is derived from at least one cell from a model organism used for studying a disease.

44. The method of claim 43, wherein the disease is a human disease.

* * * * *